United States Patent [19]

Chiarolla

[11] 4,066,079
[45] Jan. 3, 1978

[54] FILTER NEEDLE

[76] Inventor: Victor D. Chiarolla, 112 Evergreen St., Mill Valley, Calif. 94941

[21] Appl. No.: 738,616

[22] Filed: Nov. 3, 1976

[51] Int. Cl.² .............................................. A61M 5/32
[52] U.S. Cl. .................................. 128/218 N; 128/221
[58] Field of Search ....... 128/218 N, 218 NV, 218 R, 128/218 M, 220, 221, 215, 216, 214, 272; 210/322, 333, 335, 339, 343

[56] References Cited

U.S. PATENT DOCUMENTS

| 2,864,366 | 12/1958 | Miskel | 128/221 |
| 3,736,932 | 6/1973 | Satchell | 128/218 R |
| 3,757,780 | 9/1973 | Ishikawa | 128/218 N |
| 3,859,999 | 1/1975 | Ishikawa | 128/218 N |

Primary Examiner—John D. Yasko
Attorney, Agent, or Firm—Alvin E. Hendricson

[57] ABSTRACT

A simple device which attaches to an injection syringe for preventing possible contaminants in a fluid drawn into the syringe from being expelled therefrom into an intravenous solution, for example. The device hereof is simply comprised as a needle holder adapted for removable attachment to a syringe barrel for accepting the flow of a liquid into the syringe during loading of same and which automatically filters such liquid dispensed from the syringe through the needle.

5 Claims, 5 Drawing Figures

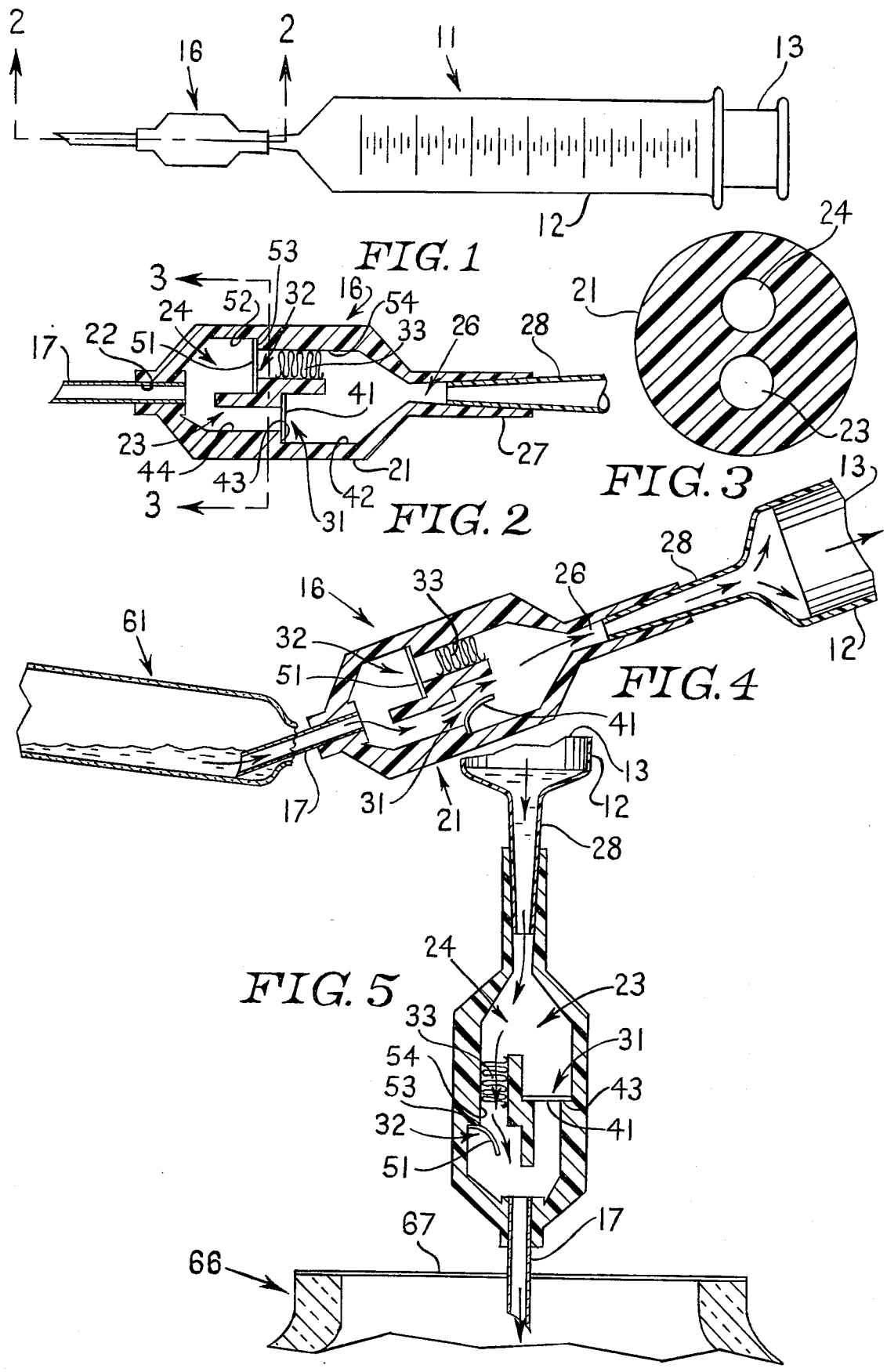

FILTER NEEDLE

BACKGROUND OF THE INVENTION

It has long been recognized that a syringe employed for withdrawing a liquid from an ampule or the like and ejecting such liquid into a medical solution such as an intravenous solution may also inject contaminants into the solution which may then be introduced into the blood stream of a person. At least as early as 1920 there was proposed in U.S. Pat. No. 1,363,128 an improvement in "Injection syringe" for the purpose of eliminating or at least minimizing the danger of drawing a contaminant into a human body so as to guard against "suppuration or any other detrimental effect." This problem has, however, persisted and more modern solutions thereof may be found in recently issued patents such as U.S. Pat. Nos. 3,736,932 and 3,938,513, for example. These latter devices and those of similar kind employ movable needle mounting, for example, or particularly constituted or configured filters which limit their widespread applicability.

There exists a need for a very simple and inexpensive unit for filtering all fluids expelled from an injection syringe, so as to positively preclude ejection of filterable contaminants therefrom. Furthermore, such a unit should require no separate operation or manipulation for the human persons employing syringes in filling and ejecting fluids therefrom may otherwise fail to employ the safeguard so that no practical advantage results therefrom.

The present invention provides a remarkably practicable solution to the problems identified above, and may be employed even by untrained personnel to produce truly superior protection of the person being administered a fluid from a syringe unit including the present invention.

SUMMARY

The present invention is provided as a physically small unit or device which removably attaches to the head of a syringe in conventional manner and which carries a forwardly extending needle. The physical aspects of the present invention are thus substantially identical to conventional disposable needle units. In addition, the present invention provides for automatically filtering fluid ejected by the syringe through the needle mounted therein irrespective of the volume of fluid which may be introduced into the syringe.

The unit of this invention is adapted to carry a forwardly projecting hollow needle and to sealingly engage the front of a syringe, all in relatively conventional manner of disposable needle mounting or attachment to a syringe. Within the unit of the present invention there is very simply provided a first passage leading from the inner end of the needle to the syringe and normally closed by a one-way valve admitting fluid flow only from the needle to syringe. Within the unit there is also provided a second passage extending from the forward or outlet end of the syringe to the needle and including not only a one-way valve admitting of fluid flow only from syringe to needle, but also a filtering material in such second passage.

BRIEF DESCRIPTION OF FIGURES

The present invention is illustrated as to one particular preferred embodiment thereof in the accompanying drawing, wherein:

FIG. 1 is a side elevational view of a syringe having a detachable needle mounting unit which may incorporate the present invention;

FIG. 2 is a longitudinal sectional view in the plane 2—2 of FIG. 1 through the unit removably connecting a needle to the syringe proper;

FIG. 3 is a transverse sectional view taken in the plane 3—3 of FIG. 2; and

FIGS. 4 and 5 are illustrations in the plane of FIG. 2 illustrating syringe operations to draw fluids therein and to discharge fluids therefrom, respectively.

DESCRIPTION

The present invention is particularly adapted to employment with a conventional syringe 11 as shown in FIG. 1. The syringe 11 includes a barrel 12 within which there is disposed a longitudinally movable plunger or piston 13 that may be manually operated by withdrawal to draw a fluid into the barrel at a front opening and by depression to expel fluid from the front of the barrel. Conventional practice provides a disposable mounting unit 16 which is adapted for removable attachment to the forward end of the syringe barrel 12. The unit 16 conventionally carries a hollow needle 17 extending axially forward therefrom and communicating with the front end of the syringe barrel. It will be appreciated that the retraction of the plunger 13 in the syringe 11 will produce a suction at the needle 17 so as to draw a fluid contacted by the needle 17 into the barrel of the syringe. Subsequently, physical depression of the plunger 13 in the barrel 12 of the syringe 11 will cause a fluid disposed in such barrel to be forced outwardly therefrom through the adapter 16 and thence through the needle attached thereto.

Conventional operation of an injection or hypodermic syringe provides for loading or filling thereof by drawing a fluid therein through the needle, as described above. It has long been recognized that fluid drawn into a syringe may possibly contain contaminants which may thus be drawn into the syringe and subsequently discharged through the syringe needle into an intravenous (IV) solution, for example. Injection of contaminants of any type or kind into an IV solution and thus eventually into the blood stream, for example, is at least injurious and may prove to be fatal. The present invention precludes this possibility with apparatus that is quite inexpensive and even more importantly is operated in exactly the same manner as conventional syringes so that the likelihood or even possibility of human error or laxness will not reduce the effectiveness of the invention.

Referring again to the drawing, there will be seen to be shown in FIGS. 2 and 3 a preferred embodiment of the present invention incorporated in the adapter 16.

The adapter 16 includes a housing or body 21 having a small diameter aperture or bore 22 extending therein from the front end of the adapter and dimensioned to receive and retain the rear end of the hollow needle 17. Within the body 21 the bore 22 branches into two relatively parallel passages 23 and 24 which extend to a rear opening 26 in the housing.

A hollow cylindrical portion 27 extends from the rear of the housing 21 with the opening 26 conically expanding through this portion to receive a hollow conical forward extension 28 of the syringe barrel 12. The adapter and syringe are removably joined by this mating conical or tapered connection which is commonly termed a lure lock. Alternative connections may be made; however, the one shown and described is conventional and is commonly employed by those employing disposable needles with syringes.

The adapter of the present invention provides one passage 23 for drawing fluid into the syringe and a second passage 24 for ejecting fluid from the syringe. This directed flow is herein achieved by providing a one-way or check valve 31 in the passage 23 wherein such valve admits of fluid flow only into the syringe barrel and positively prevents fluid flow in the opposite direction through the passage 23. In the passage 24 there is also provided a one-way check valve 32 which admits of fluid flow out of the syringe barrel but positively prevents fluid flow into the syringe. In accordance with the present invention there is also provided a fluid filter 33 in one of the adapter passages 23 or 24 and the filter is shown to be preferably disposed in passage 24 on the syringe side of the valve 32. By the illustrated location of the filter 33 maximum protection is afforded by the present invention, inasmuch as any and all fluid forced into the needle from the syringe must then pass through the filter for removal of any contaminants. This filter location will be seen to provide for removal even of contaminants that might have resided in the syringe barrel before the fluid was drawn therein for ejection.

The valves 31 and 32 may be formed as shown in FIG. 3, and referring to valve 31, it will be seen to be comprised as a disc 41 disposed in an expanded portion 42 of the passage 23 and normally resting against an annular shoulder 43 between the expanded portion 42 of the passage and a portion 44 of lesser diameter. The larger or expanded portion 42 of the passage extends from the rear opening 26 to the shoulder 43 and the small portion 44 extends therefrom to the front bore 22 in the adapter body 21. The disc 41 is mounted to pivot or bend away from the shoulder 43 as indicated, for example, in FIG. 4. One part of the edge or periphery of the disc is secured to the wall of the passage portion 42 or to the shoulder 43 and the disc may be flexible to bend, as shown. The disc 41 normally seats against the shoulder 43 so as to close the passage 23 as illustrated in FIG. 3. Any pressure exerted to the left on the disc 41 as shown in FIG. 2, i.e., away from the syringe end of the adapter, will only more tightly seal the disc 41 against the shoulder 43. On the other hand a suction applied to the right side of the disc 41 as shown in FIG. 2, as by retraction of a syringe plunger, will cause the disc 41 to pivot or bend away from the shoulder 43 to admit fluid flow through the valve 31.

The other valve 32 may be likewise formed by a disc 51 disposed in an expanded portion 52 of the passage 24 communicating with the needle bore 22 and normally disposed in sealing engagement with a shoulder 53 about the inner end of the expanded portion 52 and a smaller portion 54 of the passage 24 extending into communication with the rear opening 26. The valve 32 is operable to pass a fluid under pressure from the syringe 11 to the needle 17 as by deflection or pivoting of the disc 51 and to positively prevent fluid flow in the opposite direction.

It will be appreciated that the one-way valves of the present invention may be formed in a variety of different ways and the illustrated and described structure is only exemplary although advantageous. It is also possible to form the adapter housing in a variety of different ways and from various different materials. The preferred embodiment of the invention illustrated is formed of a plastic material that may, for example, be molded as separate halves and joined together after valve disc insertion.

Operation of the present invention is quite clear from the foregoing description of the elements of a preferred embodiment of the invention. There are, however, illustrated in FIGS. 4 and 5 the operations of the present invention during filling or loading of a syringe equipped with the present invention, and discharge of fluid therefrom as by injection of a medicament into a bottle containing an IV solution, for example. FIG. 4 shows the position and relation of elements hereof during the drawing of fluid into a syringe, as from an ampule 61 that has had the top thereof broken off in conventional manner to provide access to the fluid therein. Such an ampule may inadvertently contain small shards of glass from breaking the top therefrom, for example. Suction in the passage 23 produced by drawing the plunger 13 rearwardly in the syringe 11 causes the disc 41 of the valve 31 to be deflected or pivoted away from the shoulder or valve seat 43, as shown in FIG. 4, to open the passage 23 to the flow of fluid from the ampule into the syringe. This fluid flow is indicated by the arrows in FIG. 4 and it will be seen that the aforementioned suction serves to even more tightly seal the valve 32 in the passage 24 so that no fluid can traverse this passage.

Discharge of a fluid from a syringe equipped with the present invention is illustrated in FIG. 5 wherein the plunger 13 of the syringe is being forced into the barrel as indicated by the large arrow and fluid pressure is thus being exerted in the upper ends of the adapter passages 23 and 24. Pressure applied above valve 31 in passage 23 will tightly seal the valve disc 41 against the shoulder or valve seat 43. Pressure applied above valve 32 in passage 24 will pivot or deflect the disc 51 of the valve 32 away from the shoulder or valve seat 53 to open this passage for the discharge of fluid therethrough to and thence through the needle 17. Fluid forced under pressure through adapter passage 24 must pass through the filter 33 which removes any and substantially all foreign particles from the fluid. The filter 33 may be comprised of a wide variety of different porous materials through which a fluid may be forced and which has the property of entrapping and retaining solids that may be carried by the fluid forced therethrough. It will be appreciated that the material of filter 33 need not be provided as a dimensionally stable element nor need the filter have any particular structural properties other than the general capability of filling the entire cross section of the passage 24 in order to insure that all fluid discharged from the syringe is, in fact, filtered. The filter 33 may, for example, be comprised simply of a fibrous material such as cotton or cellulosic material "stuffed" into the passage 24 and generally the filter may be most easily inserted in the upper portion 54 of the passage 24, as shown.

The present invention, as described above, will be seen to provide a simple but highly effective system for preventing the injection of impurities or foreign bodies into an IV solution or a human being, for example. In FIG. 5 the syringe needle 17 is shown to be inserted into an IV bottle 66 through a diaphragm 67 disposed across the top thereof as an example, and the needle might also be inserted into the body of a person. Even a minute particle entrained in the fluid injected into the body of a person may be seriously injurious or even fatal, and the present invention positively precludes this occurrence. Of further importance is the certainty of use and proper operation of the present invention to thus insure attainment of the desired result despite the presence of human error and resistance to change. Although relatively trained personnel normally are employed to fill injection syringes with fluids and to inject fluids with such syringes, it is well known that the human being is resistant to change and is prone to error in executing normal operations wherein minor changes from normal may be required. These problems are now existent in the field of the present invention wherein prior art devices intended to produce the same or similar results as the present invention fail to do so because of the human factor. Failure to take certain actions or to make certain necessary adjustments or the like may and in fact does result in failure to properly filter fluids injected into IV solutions, for example in doctors' offices and hospitals.

The present invention, on the other hand, is entirely "invisible" to the user. A technician, pharmacist, vocational nurse, registered nurse or even a medical doctor may fail to follow particular deviations in long established procedures which would ensure complete filtration of all fluids injected with prior art devices. The present invention ensures complete filtration without the operator in any way deviating from normal or standard operating procedures and in fact without any discernible change of equipment so that the operator "automatically" produces the proper results. It is indeed a practical and highly useful result that is achieved by the present invention.

The present invention has been illustrated and described with respect to a particular preferred embodiment hereof; however, it is not intended to limit the invention to the precise terms of description or details of illustration, for it will be apparent to those skilled in the art that numerous variations and modifications may be made within the spirit and scope of the invention.

What is claimed is:

1. An improved filter device for an injection syringe which has a plunger disposed in a barrel for drawing a fluid into the barrel through a front opening and ejecting such fluid therefrom by plunger movement comprising:

a housing having a syringe receiving rear opening at the rear thereof for engagement with a syringe about the front opening thereof and a needle receiving aperture at the front thereof for engaging a hypodermic needle in extension therefrom, said housing defining first and second separate passages extending between said rear opening and front aperture thereof, a first one-way valve disposed in said first passage for admitting the flow of fluid therethrough only from said aperture to said opening, a second one-way valve disposed in said second passage for admitting the flow of fluid therethrough only from said opening to said aperture, and filter material disposed in one of said passages on the inlet side of the valve therein.

2. The filter device of claim 1 further defined by said filter material being disposed in said second passage.

3. The filter device of claim 1 further defined by said second valve being disposed at an end of said second passage adjacent said aperture.

4. The filter device of claim 1 further defined by each of said passages having an internal shoulder thereabout serving as a valve seat and each of said valves including a disc configured to substantially fit the internal cross sectional configuration of the respective passage and secured to the housing in such passage for movement into and out of seating engagement with the shoulder therein.

5. The filter device of claim 1 further defined by said housing having a rear projection with said rear opening extending therethrough and conically expanding rearwardly to mate with a tapered front end of a syringe for removable engagement therewith, and said device having a hypodermic needle permanently fixed in said aperture and extending from said device.

* * * * *